United States Patent [19]

Rovnyak et al.

[11] 4,053,613
[45] Oct. 11, 1977

[54] 1,3,THIAZOLINYL AND 1,3 THIAZINYL SUBSTITUTED INDOLINONES

[75] Inventors: George C. Rovnyak, Hopewell; Venkatachala Lakshmi Narayanan, Hightstown; Rudiger D. Haugwitz, Titusville, all of N.J.

[73] Assignee: E. R. Squibb & Sons, Inc., Princeton, N.J.

[21] Appl. No.: 614,393

[22] Filed: Sept. 17, 1975

[51] Int. Cl.² .................. A61K 31/425; A61K 31/54; C07D 417/04; C07D 417/14
[52] U.S. Cl. .............................. 424/246; 260/306.7 T; 260/325 R; 260/326.16; 544/54; 424/270
[58] Field of Search ................ 260/306.7 R, 306.7 T, 260/243 R; 424/246, 270

[56] References Cited
U.S. PATENT DOCUMENTS 3,755,316  8/1973  Narayanan et al. .......... 260/306.7 T
3,873,559  3/1975  Narayanan et al. .......... 260/306.7 T
4,002,749  1/1977  Rounyak ...................... 260/306.7 T Primary Examiner—Alton D. Rollins
Assistant Examiner—David E. Wheeler
Attorney, Agent, or Firm—Lawrence S. Levinson; Merle J. Smith; Burton Rodney

[57] ABSTRACT

Indolinone compounds which exhibit anti-inflammatory activity have the following formula

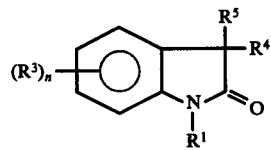

wherein $R^1$, $R^3$, $R^4$, $R^5$, and $n$ are as defined herein.

16 Claims, No Drawings

1,3,4,5,15,THIAZOLINYL AND 1,3 THIAZINYL SUBSTITUTED INDOLINONES

The present invention relates to thiazolinyl and thiazinyl derivatives of indolinones having the structure

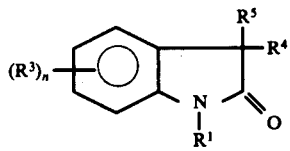

wherein
R[1] is

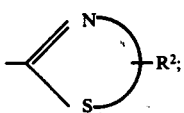

R[2] is hydrogen, lower alkyl, aryl or lower alkylaryl;
R[3] is hydrogen, lower alkyl, trifluoromethyl, halo, amino, lower alkoxy, nitro, cyano, acyl, aroyl or dilower alkylamino;
R[4] is hydrogen or

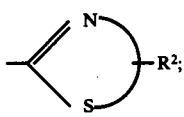

R[5] is hydrogen, arylmethyl or substituted arylmethyl; and n is 1 or 2.
The radical

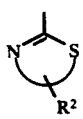

represents a 5- or 6-membered ring containing three or four carbons, respectively, wherein the additional two or three carbons (not shown) may include a substituent other than hydrogen as indicated above.

The lower alkyl groups represented by the above R groups include straight or branched chain aliphatic hydrocarbon radicals having up to seven carbon atoms, such as methyl, ethyl, propyl, isopropyl, butyl, isobutyl, t-butyl, amyl, hexyl, heptyl, and the like.

The lower alkoxy group can be represented by the formula lower alkyl—O— and this includes straight and branched chain radicals of up to and including seven carbon atoms, corresponding to the above alkyl groups, e.g., methoxy, ethoxy, propoxy, isopropoxy, and the like.

The term "halogen" includes each of the four halogens, but fluorine and chlorine are preferred.

Examples of the di-lower alkyl amino group wherein lower alkyl is defined herein include dimethylamino, diethylamino, ethylmethylamino, butylmethylamino, ethyl i-propylamino and the like.

The term "aryl" includes moncyclic or bicyclic monovalent aromatic ring systems such as phenyl or naphthyl.

The term "arylmethyl" or "substituted arylmethyl" includes aryl groups as defined above attached to a methylene group, the substituted radical including one or more substituents such as halogen, lower alkyl, nitro, trifluoromethyl, and lower alkoxy.

The term "lower alkyl aryl" represents an aryl group substituted with a lower alkyl group as defined above.

The acyl and aroyl groups included herein are derived from hydrocarbon carboxylic acids of less than twelve carbon atoms, which may be exemplified by the lower alkanoic acids (e.g., formic, acetic, propionic, butyric, valeric, trimethyl acetic and caproic acids), the lower alkenoic acids (e.g., acrylic, methacrylic, crotonic, 3-butenoic and senecioic acids), the monocyclic arylcarboxylic acids (e.g., benzoic and toluic acids), the monocyclic aryl-lower alkanoic acids [e.g., phenacetic, β-phenylpropionic, α-phenylbutyric, and 5-(p-methylphenyl) pentanoic acids], the cycloalkyl carboxylic acids (e.g., cyclobutane carboxylic acid, cyclopentane carboxylic acid and cyclohexane carboxylic acid), the cycloalkenyl carboxylic acids (e.g., 2-cyclobutene carboxylic acid and 3-cyclopentene carboxylic acid), the cycloalkyl and cycloalkenyl-lower alkanoic acids [e.g., cyclohexaneacetic, α-cyclopentanebutyric, 2-cyclopenteneacetic and 3-(3-cyclohexene)pentenoic acid], and the like. Thus the above acyl and aroyl groups may be represented by the formula

wherein R may be lower alkyl, lower alkenyl, aryl, aryl-lower alkyl, cycloalkyl, cycloalkenyl, cycloalkyl-lower alkyl, and cycloalkyl-lower alkenyl.

Thus, compounds of formula I can have the following structures

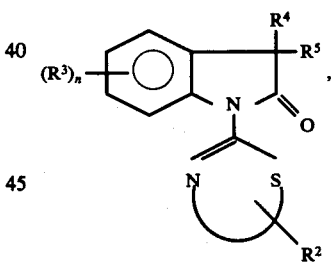

II

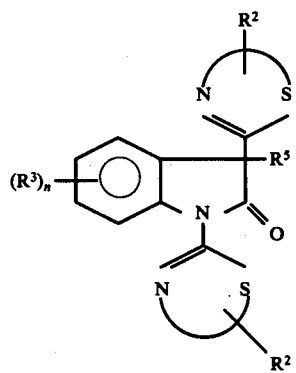

III

Preferred are those compounds of formula II wherein R[2], R[3], R[4] and R[5] are hydrogen and

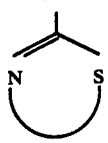

is a 5- or 6-membered ring and compounds of formula III wherein $R^2$ and $R^3$ are hydrogen, $R^5$ is phenylmethyl or hydrogen and

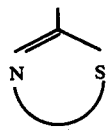

is a 5- or 6-membered ring. The compounds of the present invention can be prepared as follows.

Compounds of formula II wherein $R^4$ and $R^5$ are hydrogen are prepared by reacting compounds of formula IV with a haloalkyl isothiocyanate of formula V in a molar ratio of from 2:1 to 1:10 in the presence of a base such as sodium hydride in a non-polar aprotic solvent such as glyme, toluene or tetrahydrofuran, at or near the reflux temperature for from 1 to 24 hours, to form a compound of formula II, in accordance with the following reaction

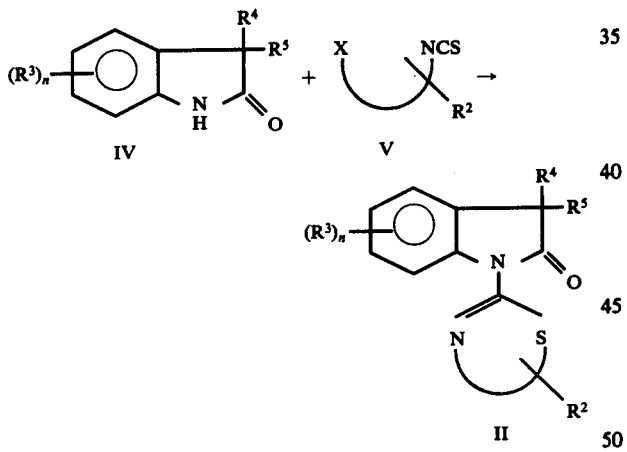

wherein $R^4$ and $R^5$ are hydrogen, X is Cl or Br and the portion

(which links N and X) in structure II represents a chain of two or three carbons, one carbon of which may include the $R^2$ substituent other than hydrogen.

Compounds of formula II, wherein $R^4$ and $R^5$ are hydrogen, can also be prepared by treating compounds of formula VI with Raney nickel in non-polar aprotic solvent such as toluene at or near the reflux temperature for from 0.5 to 24 hours.

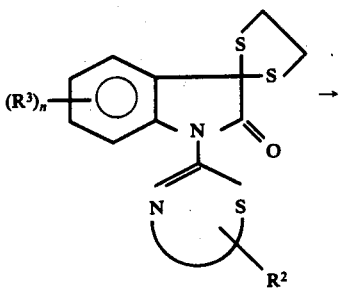

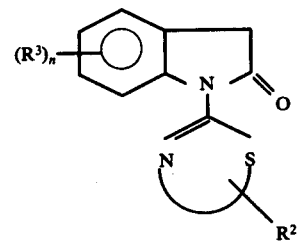

Compounds of formula VI can be prepared by reacting compounds of formula VII with an α,ω-alkanedithiol of formula VIII such as 1,2-ethanedithiol, using conditions described in the literature [HOAC, BF$_3$OEt$_2$; J.A.C.S., 80, 5575 (1958)].

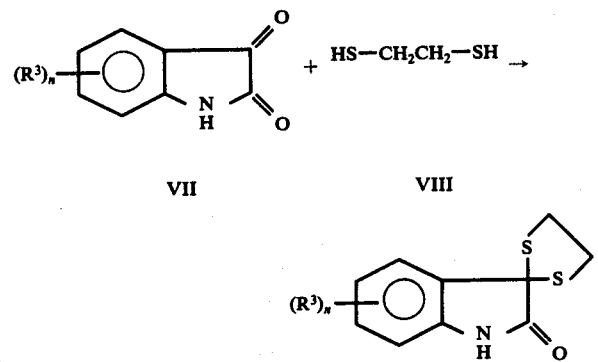

Compounds of formula IX can then be reacted with a haloalkyl isothiocyanate of formula V under the conditions as described above to give compounds of formula VI.

Compounds of formula III wherein $R^5$ is hydrogen can be prepared as co-products of the corresponding compounds as described above (under the first mentioned method for preparing compounds of formula II), but can preferentially be formed when the reaction is performed in a polar aprotic solvent such as dimethylformamide and with a base such as thallium ethoxide or potassium carbonate.

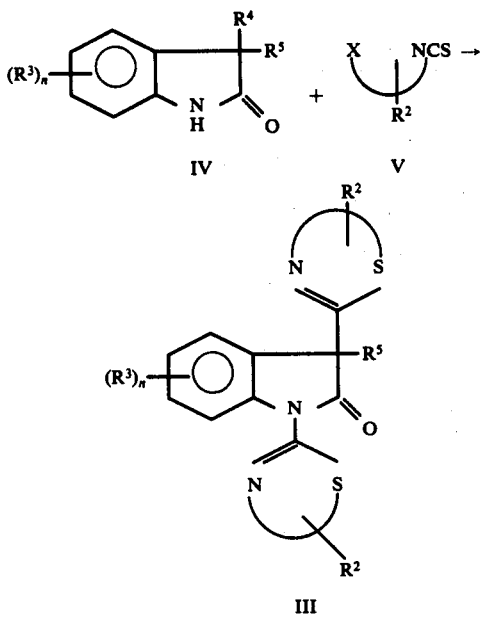

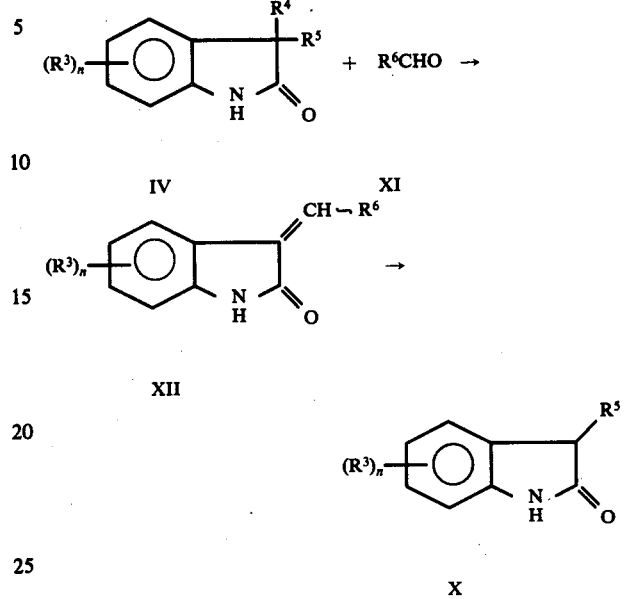

Compounds of formula III, wherein $R^5$ is arylmethyl, can be prepared by reacting a compound of formula X with a haloalkyl isothiocyanate V in a ratio of from 1:2 to 1:3, in the presence of a base such as sodium hydride, in a non-polar aprotic solvent such as glyme, toluene or tetrahydrofuran, at or near the reflux temperature for from 0.5 to 12 hours.

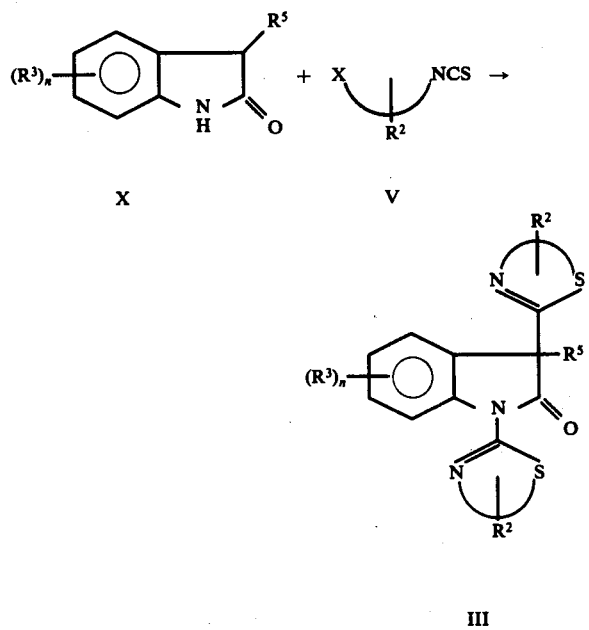

Compounds of formula X, wherein $R^5$ is arylmethyl, are prepared by reacting a compound of formula IV wherein $R^4$ and $R^5$ are hydrogen with an aldehyde of formula XI, wherein $R^6$ is aryl, in a molar ratio of from 1:1 to 1:2, in the presence of a base such as piperidine, in a non-polar aprotic solvent such as benzene, at or near the reflux temperature for from 0.5 to 24 hours to give a compound of formula XII, which in turn, is reacted with hydrogen, in the presence of a catalyst such as palladium on carbon in a solvent such as ethyl acetate at atomspheric pressure and ambient temperature for from 4 to 24 hours.

wherein $R^6$ is aryl or substituted aryl.

Where in the compounds of the invention $R^3$ is nitro, the nitro group may be reduced by conventional means to amino.

A variety of nuclear substituted oxindole derivatives are available. General methods of syntheses are reviewed in several texts:

1. The Chemistry of Heterocyclic Compounds A. Weissberger, ed. Vol. 8 Interscience Publishers, Inc., N.Y. (1954)
2. Heterocyclic Compounds R. C. Elderfield Vol. 3 John Wiley & Sons, Inc., N.Y. (1952)
3. The Chemistry of Indoles R. J. Sundberg Academic Press, N. Y. (1970)

In addition, articles by P. G. Gassman outline another general method of synthesis of oxindoles.

1. J.A.C.S. 96 5508 (1974).
2. J.A.C.S. 96 5512 (1974).

The compounds of formula I form physiologically acceptable acid-addition salts with inorganic and organic acids. These acid-addition salts frequently provide useful means for isolating the products from reaction mixtures by forming the salt in a medium in which it is insoluble. The free base may then be obtained by neutralization, e.g., with a base such as sodium hydroxide. Then any other salts may again be formed from the free base and the appropriate organic or inorganic acid. Illustrative are the hydrohalides, especially the hydrochloride and hydrobromide which are preferred, sulfate, nitrate, phosphate, oxalate, tartrate, maleate, fumerate, citrate, succinate, methanesulfonate, benzenesulfonate, toluenesulfonate, and the like.

The compounds of the invention are useful as antiinflammatory agents and are effective in the prevention and inhibition of granuloma tissue formation in warm blooded animals, and may be used, for example, in a manner similar to phenylbutazone or indomethacin. They may be used to decrease joint swelling, tenderness, pain and stiffness in mammalian species, such as dogs and monkeys, e.g., in conditions such as rheumatiod arthritis. Compounds of formula I or a physiologically acceptable acid-addition salt thereof may be compounded for such use according to accepted pharmaceutical practice in oral dosage forms such as tablets, capsules, elixirs or powders for administration of about 100 mg to 2 gm per day, preferably 100 mg to 1 gm per day in two to four divided doses. de The following Examples further illustrate and represent preferred embodiments of the invention. All temperatures are expressed in ° C.

EXAMPLE 1

1-(2-Thiazolin-2-yl)-2-indolinone

To a solution of 4.0 g (0.03 mole) of oxindole in 125 ml dry glyme there is added 1.4 g (0.03 mole) of sodium hydride (50% oil dispersion) and the mixture is stirred at room temperature for 3 hours. 3.6 g (0.3 Mole) of 2-chloroethyl isothiocyanate in 5 ml of dry glyme is then added and the mixture is refluxed overnight. After evaporation of the solvent in vacuo, the residue is chromatographed on an Alumina Act. IV column. Elution with ethyl ether yields the product which is crystallized from ethyl ether to yield 0.6 g, m.p. 97°–99°.

EXAMPLE 2

1-(2-Thiazolin-2-yl)-2-indolinone

A. Ethylene thioketal of isatin

The ethylne thioketal of isatin is prepared by the method described in J.A.C.S., 80, 5575 (1958). To a hot (95°) solution of isatin (44 g, 0.3 mole) and 1,2-ethanedithiol (30 ml) in 450 ml of acetic acid there is added 30 ml of boron trifluoride etherate. The solution is then allowed to cool slowly to room temperature. The product is collected and washed well with acetic acid and with water and dried in vacuo at 60°to give 48.9 g: m.p. 198°–200°.

B. (4,5-Dihydro-2-thiazolyl)-4,5-dihydrospiro[[1,3]-dithiole-2,3'-[3H]indol]-2'(1'H)-one To a slurry of NaH (2.88 g, 0.12 mole) in dry tetrahydrofuran (100 ml) under N₂ at room temperature there is added a solution of the ethylene thioketal of isatin (22.3 g, 0.1 mole) in dry tetrahydrofuran (250 ml). The solution is then warmed to 50° for 1 hour. At room temperature there is added a solution of 2-chloroethyl-isothiocyanate (13.3 g, 0.11 mole) in dry tetrahydrofuran (50 ml). After stirring for 0.5 hour at room temperature, the solution is heated at reflux temperature for 4 hours. The mixture is filtered and the solids are washed (CHCl₃). The combined filtrate and washings are concentrated in vacuo, and the residue is dissolved in CHCl₃ and washed with water (2X). The organic fraction is dried (CaCl₂), treated with Darco and concentrated in vacuo. The residue is crystallized twice from CHCl₃/methanol to give (4,5-Dihydro-2-thiazolyl)-4,5-dihydrospiro[[1,3]dithiole- 2,3'-[3H]indol]-2'(1'H)-one (19.6 g, 63.5%), m.p. 154.5°–157°.

C. 1-(2-Thiazolin-2-yl)-2-indolinone

The compound obtained in part B is treated with activated Raney nickel in refluxing toluene for 5 hours, giving upon removal of catalyst and evaporation o the solvent a product identical to that obtained in Example 1.

EXAMPLE 3

1,3-bis(2-thiazolin-2-yl)-2-indolinone

Further elution of the Alumina column from Example 1 with CHCl₃ yields a yellow oil which is crystallized from CHCl₃ to yield 1.1 g, m.p. 204°–205°.

EXAMPLE 4

1,3-Bis(2-thiazolin-2-yl)-2-indolinone

When the reaction between oxindole and 2-chloroethylisothiocyanate, as described in Example 1, is performed in the presence of either potassium carbonate or thallium ethoxide in dimethylformamide, 1,3-bis(2-thiazolin-2-yl)-2-indolinone, identical in all respects to that obtained in Example 3, is formed preferentially.

EXAMPLE 5

1,3-Bis(4,5-dihydro-2-thiazolyl)-1,3-dihydro-3-(phenylmethyl)-2H-indol-2-one Method A To a stirred suspension of sodium hydride (1.2 g, 48 mmole) in dry tetrahydrofuran (70 ml) is added dropwise a solution of 3-phenylmethyl indolin-2-one (4.5 g, 20 mmole) [prepared from oxindole (49.5 g, 0.37 mmole), benzaldehyde (50 ml, 0.5 mole) and piperidine (2 ml) in 500 ml of benzene, heated at reflux temperature with separation of water; intermediate product, obtained by crystallization from ethanol to give 69.6 g; m.p. 177°–179°, is hydrogenated in ethyl acetate at room temperature and atmospheric pressure over Pd/C catalyst to give the product: m.p. 130°–131° .]indry tetrahydrofuran (150 ml). The resultant solution is stirred at room temperature for another hour, after which it is cooled to 0° C in an ice bath and a solution of 2-chloroethylisothiocyanate (5.0 g, 40 mmole) in dry tetrahydrofuran (80 ml) is added. The mixture is heated at reflux temperature for 1.5 hours.

Solvent is removed in vacuo; the residue is brought into CHCl₃ (200 ml) and washed with diluted HCl and water (2X). The organic layer is dried (anhydrous MgSO₄) and concentrated to give 8.4 g of a semi-solid material.

This crude material is applied to a wet packed (hexane) column (150 g of neutral AL₂O₃, activity III), and eluted with 100/0–0/100 hexane/ethyl acetate.

The fractions eluted with 0/100 to 20/80 ethyl acetate/hexane are combined and crystallized from acetone/hexane to give 1.4 g of the product: m.p. 207°–208.5° C. Concentration of the mother liquor affords an additional 0.9 g, m.p. 206°–207.5° (Total yield, 30%).

Method B

To a stirred mixture of thallium ethoxide (5.6 g, 22.4 L mmole) in dimethyl formamide (100 ml) is added dropwise a solution of 3-phenylmethyl indolin-2-one (5.0 g, 22.4 mmole, prepared as in method A) in dimethyl formamide (100 ml). The resultant solution is stirred at room temperature for 2 hours. Then, an ice bath is used to cool the mixture to 0° C, and a solution of 2-chloroethylisothiocyanate (2.7 g, 22.4 mmole) in dimethyl formamide (50 ml) is added. The reaction mixture is warmed at 60° C for 20 hours.

The insoluble material from the reaction mixture is removed by filtration. The filtrate is diluted with an equal volume of cold water. This aqueous mixture, after standing at room temperature for 3 hours, precipitates out some crude product. This is collected by filtration and recrystallized from acetone/hexane to give 1.7 gm (40%) of the product, identical with that obtained in column II, the product shown in column III is obtained.

TABLE A

| | Column I | Column II | Column III | |
|---|---|---|---|---|
| Ex. No. | $R^3$(position) | | $R^3$(position) | |
| 6 | Cl(5) | SCNCH$_2$CH$_2$Br | As in column I | |
| 7 | CH$_3$(6) | " | " | " |
| 8 | H | SCNCH$_2$CHBr<br>\|<br>CH$_3$ | " | |
| 9 | H | SCNCH$_2$CHBr<br>\|<br>C$_6$H$_5$ | " | |
| 10 | H | SCNCH$_2$CH$_2$CH$_2$Br | " | |
| 11 | C$_2$H$_5$O(6) | " | " | " |
| 12 | NO$_2$(6) | " | " | " |
| 13 | CN(5) | SCNCH$_2$CH$_2$Br | " | |
| 14 | CH$_3$C(6)<br>\|\|<br>O | " | " | " |
| 15 | C$_6$H$_5$C(5)<br>\|\|<br>O | " | " | " |
| 16 | (CH$_3$)$_2$N(6) | SCNCH$_2$CH$_2$Br | " | " |
| 17 | CF$_3$(5) | " | " | " |
| 18 | Cl(5)<br>Cl(7) | SCNCH$_2$CHBR<br>\|<br>C$_6$H$_4$—3-CH$_3$ | " | |

Method A.

EXAMPLES 6 to 18

Following the procedure of Example 1 but substituting for the oxindole the compound shown in column I of Table A set out below, and substituting for the 2-chloroethyl isothiocyanate, the compound shown in column II, the product shown in column III is obtained.

EXAMPLES 19 to 29

Following the procedure of Examples 1 and 3, but substituting for oxindole the compound shown in Column I of Table B set out below, and substituting for the 2-chloroethylisothiocyanate, the compound shown in Colmun II, the product shown in Column III is obtained.

TABLE B

| | Column I | Column II | Column III |
|---|---|---|---|
| | $(R^3)_n$—indolin-2-one (NH) | SCN–(R²)–X | $(R^3)_n$—disubstituted indolin-2-one with two thiazoline-like R² groups |

| Ex. No. | R³(position) | | R³(position) | R² |
|---|---|---|---|---|
| 19 | H | SCNCH₂CHBr(CH₃) | As in column I | thiazoline-CH₃ |
| 20 | Cl(5) | SCNCH₂CH₂CH₂Br | " | 6-membered N=C–S ring |
| 21 | NO₂(6) | SCNCH₂CH₂CHBr(C₆H₅) | " | 6-membered ring with C₆H₅ |
| 22 | CH₃(5,6) | SCNCH₂CH₂Br | " | thiazoline |
| 23 | CH₃C(5)=O | " | " | " |
| 24 | CF₃(4) | " | " | " |
| 25 | CH₃O(6) | " | " | " |
| 26 | CN(5) | SCNCH₂CH₂CH₂Br | " | 6-membered ring |
| 27 | C₆H₅C(6)=O | " | " | " |
| 28 | (C₂H₅)₂N(5) | " | " | " |
| 29 | Cl(5), Cl(7) | SCNCH₂CH₂Br | " | thiazoline |

EXAMPLES 30 to 40

Following the procedure of Example 5 (Method A) but substituting for 3-phenylmethyl indolin-2-one the compound shown in Column I of Table C below, and substituting for 2-chloroethylisothiocyanate the compound shown in Column II, the compound shown in Column III is obtained.

TABLE C

| Column I | Column II | Column III |
|---|---|---|
| ![structure with (R³)ₙ, CH₂C₆H₅, N-H, =O] | SCN-X-R² | ![structure with (R³)ₙ, CH₂C₆H₅, N-thiazoline with R²] |

| Ex. No. | R³(position) | | R³(position) | |
|---|---|---|---|---|
| 30 | H | SCNCH₂CH₂CH₂Br | As in Column I | ![thiazoline ring with R²] |
| 31 | H | SCNCH₂CH₂CH₂Br with C₂H₅ | " | ![ring with C₂H₅] |
| 32 | Cl(4) | SCNCH₂CHBr with C₆H₅ | " | ![ring with C₆H₅] |
| 33 | CH₃(5,6) | SCNCH₂CH₂Br | " | ![thiazoline ring] |
| 34 | C₂H₅C(5)=O | " | " | " |
| 35 | n-C₃H₇(4) | " | " | " |
| 36 | CF₃(6) | SCNCH₂CH₂CH₂Br | " | ![6-membered ring] |
| 37 | CH₃O(5) | " | " | " |
| 38 | CN(6) | " | " | " |
| 39 | C₆H₅C(5)=O | " | " | " |
| 40 | (C₂H₅)₂N(6) | " | " | " |

What is claimed is:

1. A compound having the formula

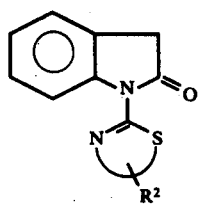

wherein R² is hydrogen, and the radical

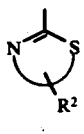

represents a 5- or 6-membered ring containing three or four carbons and one double bond; and pharmaceutically acceptable acid-addition salts thereof.

2. A compound as defined in claim 1 having the name 1-(2-thiazolin-2-yl)-2-indolinone.

3. A pharmaceutical composition comprising a compound as defined in claim 1 and a pharmaceutically acceptable carrier therefor.

4. A method of treating inflammation in mammalian species, which comprises orally administering to a mammalian host a therapeutic amount of a composition as defined in claim 3.

5. A compound having the formula

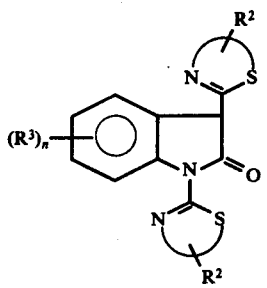 or

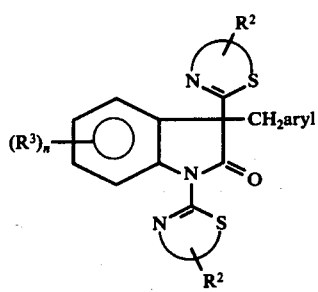

wherein R² is selected from the group consisting of hydrogen, lower alkyl, phenyl or lower alkylphenyl; R³ is selected from the group consisting of hydrogen, lower alkyl, trifluoromethyl, halo, lower alkoxy, nitro, cyano, amino, di-lower alkylamino or

wherein R contains less than 11 carbons and is selected from the group consisting of lower alkyl, lower alkenyl, phenyl, phenyl-lower alkyl, cycloakyl, cycloalkenyl, cycloalkyl-lower alkyl, and cyclo-lower alkenyl, however where n is 2, and adjacent R³ groups are present, at least one of the R³ groups is other than t-butyl, trifluoromethyl or nitro; aryl is phenyl or phenyl mono-substituted with a member selected from the group consisting of halogen, lower alkyl, nitro, trifluoromethyl, and lower alkoxy; n is 1 or 2; the radical

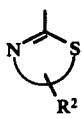

represents a 5- or 6-membered ring having three or four carbons and one double bond; and pharmaceutically acceptable acid-addition salts thereof.

6. A compound as defined in claim 5 having the formula

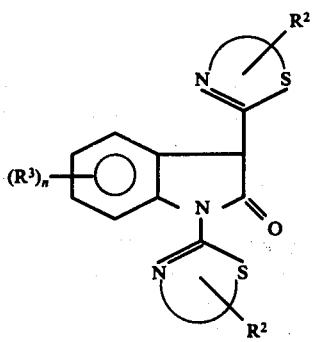

7. A compound as defined in claim 5 having the formula

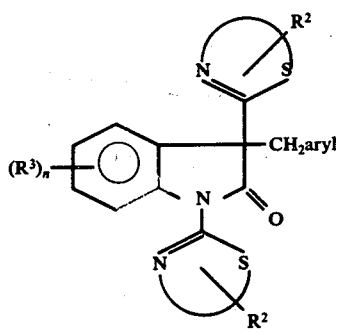

8. A compound as defined in claim 5 wherein n is 1.
9. A compound as defined in claim 5 wherein n is 2.
10. A compound as defined in claim 7 wherein R³ is H, —CH₂aryl is —CH₂C₆H₅ and

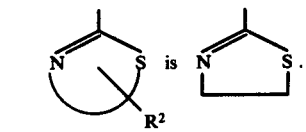

11. A compound as defined in claim 6 wherein R³ is H, and

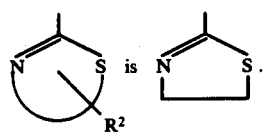

12. A compound as defined in claim 1 wherein R¹ is selected from the group consisting of

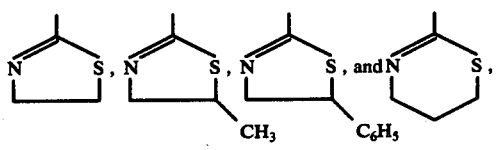

R³ is selected from the group consisting of H, halo, and lower alkyl, R⁴ is selected from the group consisting of H,

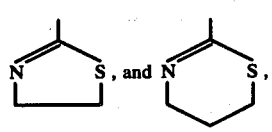

and R⁵ is selected from the group consisting of H and —CH₂C₆H₅.

13. A compound as defined in claim 5 having the name 1,3-bis(2-thiazolin-2-yl)-2-indolinone.
14. A compound as defined in claim 5 having the name 1,3-bis(4,5-dihydro-2-thiazolyl)-1,3-dihydro-3-(phenylmethyl)-2H-indol-2-one.
15. A pharmaceutical composition comprising a compound as defined in claim 5 and a pharmaceutically acceptable carrier therefor.
16. A method of treating inflammation in mammalian species, which comprises orally administering to a mammalian host a therapeutic amount of a composition as defined in claim 15.

* * * * *

UNITED STATES PATENT OFFICE
CERTIFICATE OF CORRECTION

Patent No. 4,053,613    Dated October 11, 1977

Inventor(s) George C. Rovnyak et al

It is certified that error appears in the above-identified patent and that said Letters Patent are hereby corrected as shown below:

On the Abstract page, in the title, after "1,3" first occurrence, delete the comma.
Column 1, line 1, in the title, "1,3,4,5,15" should read --1,3--.
Column 7, line 31, "ethylne" should read --ethylene--.
Column 7, line 66, "o" should read --of--.
Column 8, line 33, "indry" should read --in dry--.
Column 8, line 46, "AL$_2$O$_3$" should read --Al$_2$O$_3$--.
Column 8, line 55, before "mmole" delete "L".
Column 10, Table A, Example 18, the structures in Columns II and III should read, respectively

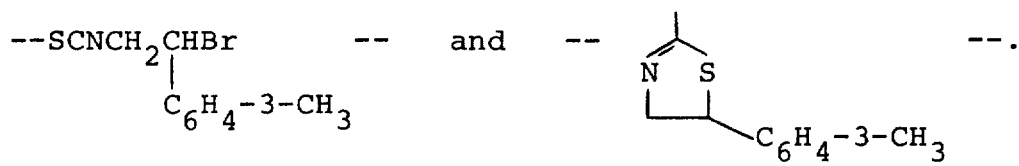   and   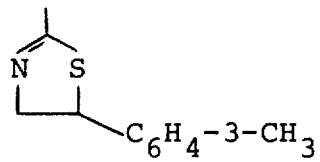   --.

Signed and Sealed this

Twenty-first Day of February 1978

[SEAL]

Attest:

RUTH C. MASON
Attesting Officer

LUTRELLE F. PARKER
Acting Commissioner of Patents and Trademarks